(12) United States Patent
Lederman et al.

(10) Patent No.: US 9,402,730 B2
(45) Date of Patent: Aug. 2, 2016

(54) FENESTRATED HUMERAL PROSTHESIS AND METHODS OF SHOULDER ARTHROPLASTY

(71) Applicant: Arthrex, Inc., Naples, FL (US)

(72) Inventors: Evan S. Lederman, Paradise Valley, AZ (US); Reuben Gobezie, Cleveland, OH (US); Gregory A. Guederian, Naples, FL (US)

(73) Assignee: Arthrex, Inc., Naples, FL (US)

( * ) Notice: Subject to any disclaimer, the term of this patent is extended or adjusted under 35 U.S.C. 154(b) by 36 days.

(21) Appl. No.: 14/181,015

(22) Filed: Feb. 14, 2014

(65) Prior Publication Data

US 2014/0288657 A1  Sep. 25, 2014

Related U.S. Application Data

(60) Provisional application No. 61/765,160, filed on Feb. 15, 2013.

(51) Int. Cl.
*A61F 2/40* (2006.01)
*A61F 2/46* (2006.01)
*A61B 17/84* (2006.01)
*A61F 2/30* (2006.01)

(52) U.S. Cl.
CPC ............ *A61F 2/4014* (2013.01); *A61F 2/4059* (2013.01); *A61F 2/4612* (2013.01); *A61B 17/842* (2013.01); *A61F 2002/3054* (2013.01); *A61F 2002/30332* (2013.01); *A61F 2002/30387* (2013.01); *A61F 2002/30471* (2013.01); *A61F 2002/30507* (2013.01); *A61F 2002/30538* (2013.01); *A61F 2002/30553* (2013.01); *A61F 2002/30784* (2013.01); *A61F 2002/4029* (2013.01); *A61F 2002/4037* (2013.01); *A61F 2002/4044* (2013.01)

(58) Field of Classification Search
CPC ..................................... A61F 2/4014
USPC ........................................ 623/19.14
See application file for complete search history.

(56) References Cited

U.S. PATENT DOCUMENTS

| | | | | |
|---|---|---|---|---|
| 6,398,812 | B1 * | 6/2002 | Masini | A61F 2/4059 623/19.14 |
| 8,323,347 | B2 | 12/2012 | Guederian et al. | |
| 2001/0011193 | A1 | 8/2001 | Nogarin | |
| 2006/0069445 | A1 * | 3/2006 | Ondrla | A61F 2/40 623/19.12 |
| 2007/0050040 | A1 * | 3/2007 | Guederian | A61F 2/4014 623/19.14 |
| 2009/0265010 | A1 * | 10/2009 | Angibaud | A61F 2/4059 623/19.11 |
| 2010/0292802 | A1 * | 11/2010 | Borowsky | A61F 2/4014 623/19.14 |
| 2012/0179262 | A1 | 7/2012 | Metcalfe et al. | |

FOREIGN PATENT DOCUMENTS

EP    0 617 934 A1    10/1994

* cited by examiner

*Primary Examiner* — David H. Willse
*Assistant Examiner* — Javier Blanco
(74) *Attorney, Agent, or Firm* — Blank Rome LLP

(57) ABSTRACT

A humeral prosthesis includes a stem component with a lateral stem body and a head component joined by an inclination component or block. The stem component and the inclination component are provided with openings/holes/fenestrations/eyelets that allow attachment of soft tissue (and optional fracture repair). A first plurality of suture holes are provided to the lateral stem body and a second plurality of suture holes are provided on the medial aspect of the inclination block. These suture holes are intended for subscapularis or lesser tuberosity reattachments. Inclination angle, radial offset, and version are adjustable and are separately and independently set and fixed.

4 Claims, 15 Drawing Sheets

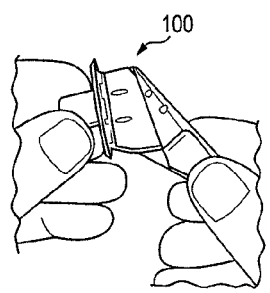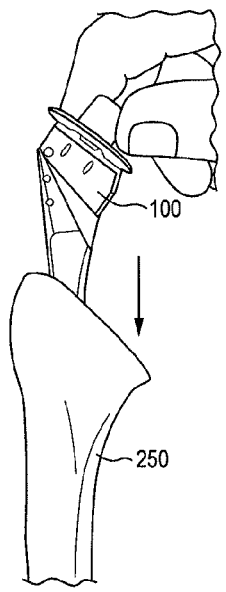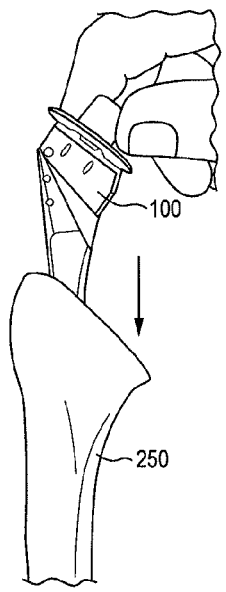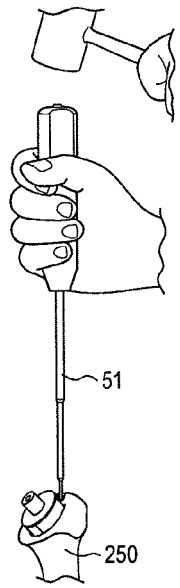
FIG. 4A
FIG. 4B
FIG. 4C
FIG. 4D

FENESTRATED HUMERAL PROSTHESIS AND METHODS OF SHOULDER ARTHROPLASTY

CROSS-REFERENCE TO RELATED APPLICATIONS

This application claims the benefit of U.S. Provisional Application No. 61/765,160 filed Feb. 15, 2013, the disclosure of which is incorporated by reference in its entirety herein.

FIELD OF THE INVENTION

The present invention relates to a shoulder arthroplasty system for surgical reconstitution of the shoulder and, in particular, to prosthetic replacement of the humerus.

BACKGROUND OF THE INVENTION

Instability and other maladies of human joints, such as arthrosis or fracture, can be sufficiently acute that prosthetic replacement of compromised joint features may be indicated. For example, in shoulder reconstruction, the humeral head may be replaced by first resecting the humeral head from the humerus and then installing a humeral prosthetic at the resection.

Various prostheses have been designed to mimic a portion of the joint, or joint region, being replaced. A shoulder prosthesis, for example, includes a stem to be anchored in the humeral canal and a hemispherical head to be positioned within the glenoid cavity of the scapula. The more-recently devised shoulder prostheses generally are modular systems which may include an articulating member (articulating inclination block component) that allows flexibility with respect to either the tilt angle or the radial offset between the head and stem.

There is a need for a shoulder arthroplasty system with suture holes provided in the articulating member (inclination piece or articulating inclination block component). Also needed is a fenestrated humeral prosthesis with suture holes that are provided in a shorter, fenestrated stem for soft tissue and fracture repairs. Also needed are methods of addressing the non-bony reattachment of the subscapularis and lesser tuberosity during a total shoulder arthroplasty. An improved modular shoulder arthroplasty system that is designed to address any or all of osteoarthritis, trauma and cuff tear arthropathy is also needed.

SUMMARY OF THE INVENTION

The present invention provides a novel prosthetic assembly for prosthetic and surgical methods for reconstitution of a joint, with special applications to the shoulder joint. The prosthetic assembly includes a fenestrated humeral prosthesis provided with a short stem having a stem body and inclination block with a plurality of holes (fenestrations or multiple suture eyelets) for subscapularis, supraspinatus and lesser tuberosity repairs.

In an exemplary embodiment, the fenestrated humeral prosthesis includes an inclination block (an articulating inclination block component) of the humeral stem that is provided with a plurality of holes (suture holes or suture eyelets). The stem is also provided with suture holes in the proximal body for soft tissue repair and subscapularis closure. The unique configuration of the suture holes/eyelets provides the user (surgeon) with more optimal and anatomical locations for subscapularis and lesser tuberosity attachment.

The present invention also provides a method of conducting surgery by providing a prosthetic assembly comprising a fenestrated humeral prosthesis with attachment points (suture holes or eyelets) for flexible material (for example, suture) provided within the body of the stem and within the articulating inclination block. A subscapularis bridge technique provides subscapularis repairs employing such suture eyelets provided within the inclination component and short stem.

Other features and advantages of the present invention will become apparent from the following description of the invention which refers to the accompany drawings.

BRIEF DESCRIPTION OF THE DRAWINGS

FIGS. 4A-4L illustrate subsequent steps of a method of shoulder repair with the humeral component of FIG. 1B.

DETAILED DESCRIPTION OF THE INVENTION

Figure 1A:
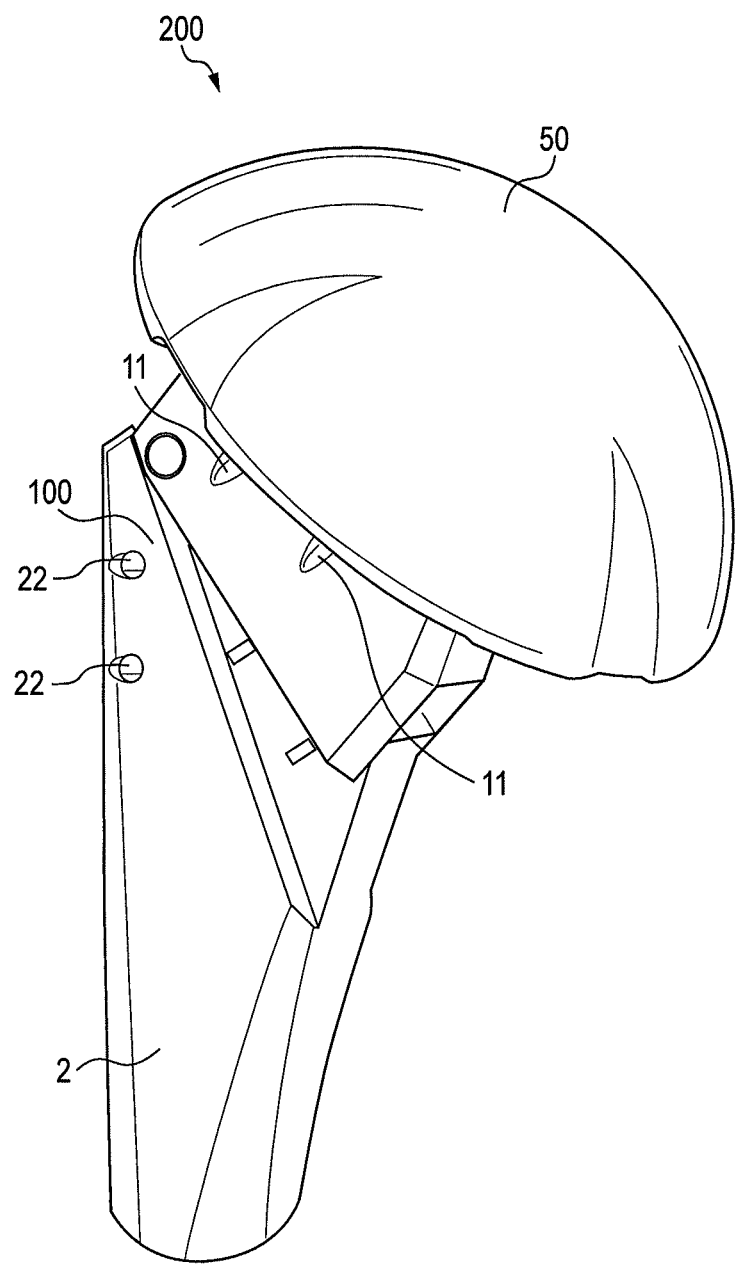
FIG. 1A illustrates an exemplary shoulder prosthesis of the present invention (provided with suture holes incorporated into stem and inclination block, for subscapularis, supraspinatus, biceps and lesser tuberosity repairs).

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the present invention.

The present invention provides a prosthetic assembly for prosthetic and surgical methods for reconstitution of a joint, with special applications to the shoulder joint. The prosthetic assembly includes a fenestrated humeral prosthesis provided with a short stem having a stem body with a plurality of holes or fenestrations (first suture holes or suture eyelets) for subscapularis and supraspinatus repairs incorporated into the short stem. The suture holes provided in the stem body preferably address soft tissue repairs and not fracture repairs. The fenestrated humeral prosthesis also includes an inclination block (an articulating inclination block component) of the humeral stem that is provided with another plurality of holes or fenestrations (second suture holes or suture eyelets). The unique configuration of the suture holes provides the user (surgeon) with more optimal and anatomical locations for subscapularis and lesser tuberosity attachment.

The present invention also provides a method of conducting surgery by providing a prosthetic assembly comprising a fenestrated humeral prosthesis with attachment points (suture holes) for flexible material (for example, suture, suture tape, suture chain or FiberWire® suture) provided within the body of the stem and within the articulating inclination block. In an exemplary embodiment, a SABER shoulder repair (Sub-scapularis Apex Bridge Repair or SABER technique) has been developed to take advantage of these suture eyelets (holes) and to incorporate subscapularis, supraspinatus and/or biceps repairs with shoulder arthoplasty.

Referring now to the drawings, where like elements are designated by like reference numerals, FIGS. 1A-7B illustrate an exemplary humeral prosthesis 200, 200a with humeral component 100, and methods of shoulder reconstruction with humeral component 100, according to exemplary embodiments of the present invention.

Figure 1B:
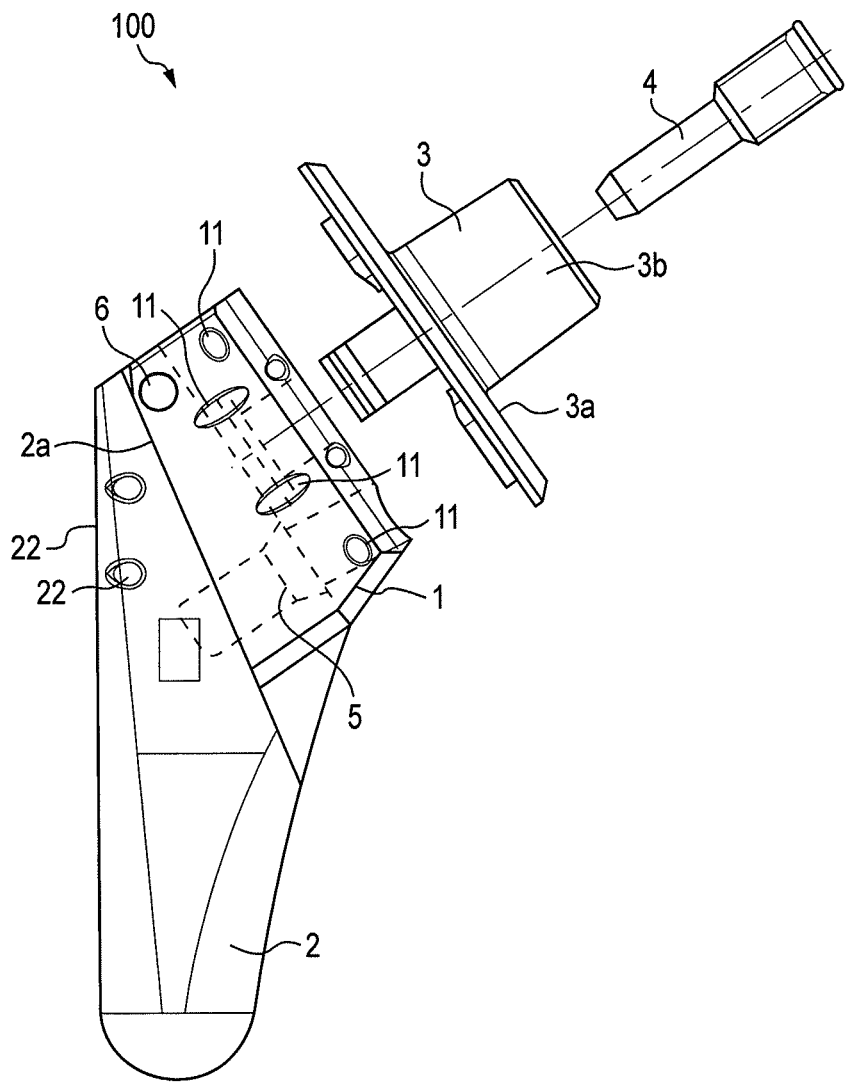
FIG. 1B illustrates an expanded view of the humeral component of the shoulder prosthesis of FIG. 1A.
Figure 1C:
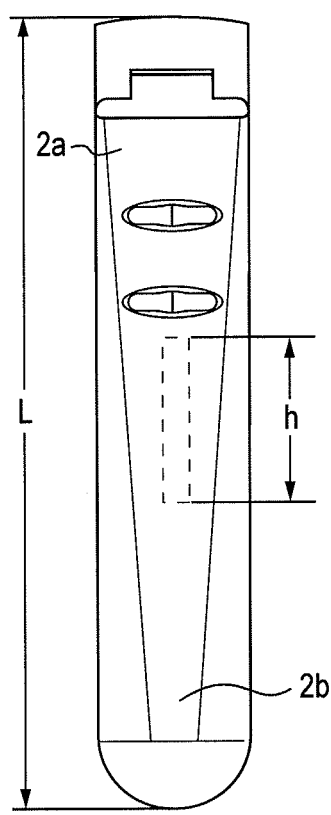
FIG. 1C illustrates a side view of the stem and inclination piece of the humeral component of FIG. 1B.

Humeral component 100 is part of a modular humeral prosthesis 200 shown in FIG. 1A in the final assembly with a spherical head 50. Humeral component 100 is detailed in FIGS. 1B-3E and includes stem 2 (stem module 2), inclination piece 1 (neck 1), trunion 3 (coupling adapter 3), version locking screw 4, inclination locking screw 5 and pin 6. Details of at least some of the elements of humeral component 100 of FIG. 1B are provided, for example, in U.S. Pat. No. 8,323,347, issued Dec. 4, 2012, the disclosure of which is incorporated by reference in its entirety herein.

As detailed below with reference to FIGS. 4A-4L, stem 2 is adapted to be introduced into a patient's humerus, the stem having a body with a length L and a width W, and a first plurality of through holes 22 (suture eyelets 22) provided laterally within the body and along the length. The inclination component 1 includes a first opening to provide access to a screw to set and fix a position of the inclination component at an inclination angle, the inclination component further including a second plurality of holes 11 (suture eyelets 11) provided within the inclination component. The coupling adapter 3 includes means for setting a version. The spherical head 50 including means for setting and fixing a radial offset, wherein the stem interfaces with the coupling adapter, and the coupling adapter interfaces with the spherical head.

Stem 2 features a shank (body) with a longitudinal axis 2b and a length L (FIG. 1C) and having an upper shank portion 2a and a pin 6 that hinges inclination component or inclination piece 1 (neck 1) to the rest of the stem module 2. Inclination component 1 fits over the upper shank portion and pivots on the pin through an inclination angle a as detailed and explained in U.S. Pat. No. 8,323,347.

Stem 2 is also provided with a first plurality of through holes 22 (first openings or fenestrations or eyelets 22) located within the upper shank portion 2a and disposed in a direction about parallel to the longitudinal axis 2b of the stem. In an exemplary-only embodiment, the first plurality of through holes 22 includes two lateral holes 22 (as shown in FIGS. 1A-1D) that allow passing of a flexible material (for example, suture) therethrough. In an exemplary-only embodiment, the first plurality of holes 22 includes suture holes or eyelets that allow suture to pass therethrough and form a suture bridge of a reinforced subscapularis repair, as detailed below with reference to FIGS. 5(a)-5(c).

The inclination component 1 (neck 1) includes an opening that provides access to a screw (shown in dotted line in FIG. 1B as inclination screw 5). The screw is advanced and locked in frictional engagement with opposing inside surfaces of the inclination component 1. The screw is advanced by turning sufficiently to fix the position of the inclination component 1 at a desired inclination angle. The inclination component 1 (neck 1) also includes an opening for engaging trunion 3 (coupling adapter 3) with version locking screw 4.

Figure 1D:
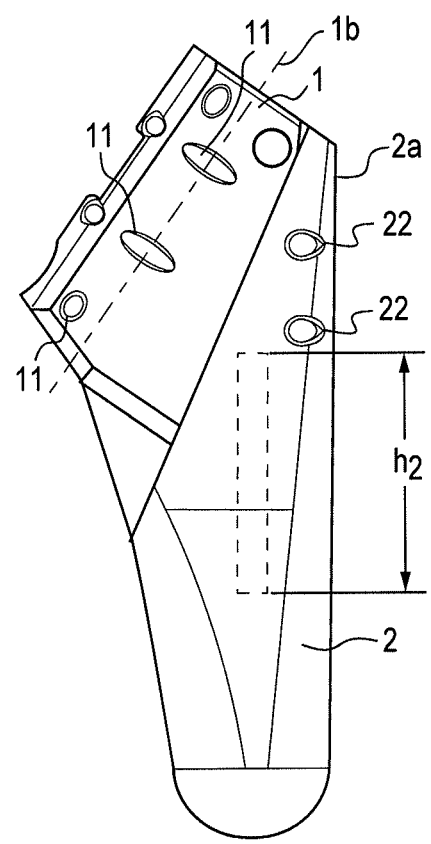
FIG. 1D illustrates a lateral view of the stem and inclination piece of FIG. 1B.
Figure 2A:
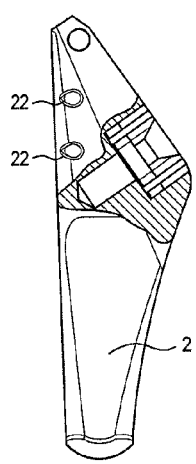
FIGS. 2A-2D illustrate additional views of the humeral stem of the prosthesis of FIG. 1A.
Figure 2B:
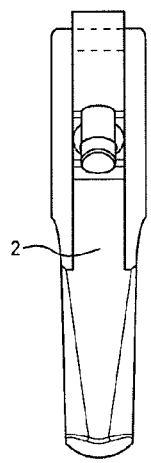
Figure 2C:
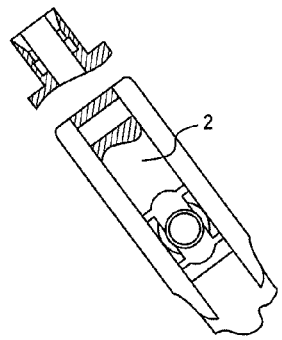
Figure 2D:
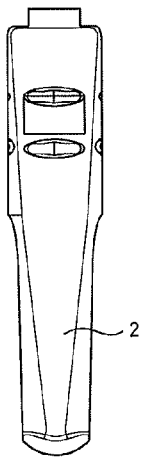
Figure 3A:
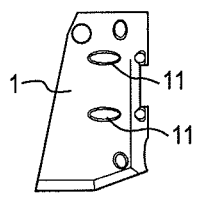
FIGS. 3A-3E illustrate additional views of the inclination piece of the prosthesis of FIG. 1A.
Figure 3B:
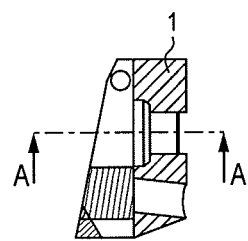
Figure 3C:
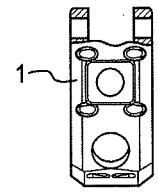
Figure 3D:
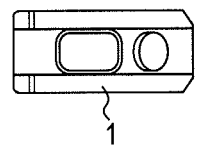
Figure 3E:
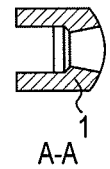

The inclination component 1 (neck 1) is further provided with a second plurality of through holes 11 (second openings or fenestrations or eyelets 11) located within the neck, as shown in FIGS. 1A and 1D, and extending in a direction about parallel to longitudinal axis 1b of the inclination component 1. In an exemplary-only embodiment, the second plurality of through holes 11 includes four holes 11 that allow passing of a flexible material (for example, four suture strands) therethrough. In an exemplary-only embodiment, the second plurality of holes 11 includes suture holes that, together with the first plurality of suture holes 22, allow multiple sutures to pass therethrough and in between and form a suture bridge of reinforced subscapularis repairs, as detailed below with reference to FIGS. 5A-5C.

Humeral component 100 also includes coupling adapter or trunion 3. The trunion or coupling adapter 3 is paired with the inclination component 1. The coupling adapter 3 includes an adapter plate 3a (shown in FIG. 1B). An access opening through the adapter plate 3a provides access to the inclination-angle locking screw 5. A male Morse taper 3b (FIG. 1B) extends from one side of adapter plate 3a. Morse taper 3b locks into a female Morse taper formed in spherical head 50 (FIG. 1A). Version is adjusted by pivoting adapter plate 3a with respect to inclination component 1. Radial offset is adjusted by rotating the spherical head 50 around male Morse taper 3b with respect to trunion 3 (coupling adapter 3). The components will pivot through different angles of retroversion and anteversion. The radial offset is fixed in position by the locking interaction of the complementary Morse taper features.

In a preferred embodiment, stem 2 provided with the first plurality of through holes 22 is a mini stem (short stem) that provides a stable subscapularis repair when is inserted into a resected humerus. In an exemplary embodiment, the mini stem 2 has a length L (FIG. 1C) of about 60 mm with two suture holes 22 for subscapularis repair and supraspinatus repair incorporated into the stem. The mini stem is designed to facilitate ease of revision and to provide a universal platform to restore/accommodate proximal humeral anatomy, as detailed below.

A method of exemplary shoulder and soft tissue repair with the prosthesis 200 of the present invention is detailed with reference to FIGS. 4A-5C below.

The humeral component 100 has a design that allows it to account for anatomical variations of the proximal humerus commonly encountered by the surgeon. Variable adjustment with respect to the inclination angle, version and head offset are features critical to reconstruction of the proximal humerus. The simplified design of the humeral component allows the surgeon to adapt the humeral stem and articular surface to the position that best represents the patient's normal anatomy. All of the adjustments can be made intraoperatively with the implant in the humeral canal. This unique feature allows the surgeon to more accurately recreate the normal anatomical relationships of the shoulder joint. With anatomic restoration of the humerus and glenoid, soft tissue balancing of the rotator cuff is more accurate, allowing for improved functional outcome. In addition, humeral stem length accounts for various anatomical and revision scenarios that may be encountered.

The implant provides at least the following features: variable inclination, version and offset; package-to-canal design (anatomic restoration in situ); eccentric humeral heads; multiple head diameters and heights for precise anatomic reconstruction; removable trunion for simplified revision; multiple suture eyelets for subscapularis and lesser tuberosity repair techniques.

A method of shoulder arthoplasty according to the present invention comprises inter alia the steps of: perform a free cut by the surgeon along the margins of the proximal humerus articular surface while maintaining the patient's articular inclination and version; release the subscapularis; release the anterior and inferior glenohumeral capsule; resect the humeral head; expose the glenoid; prepare the humeral head; prepare the glenoid and implant the keel glenoid implant; prepare the glenoid and implant the pegged glenoid; implant the humeral stem; and close the wound by attaching soft tissue to the humeral stem and inclination component (employing eyelets 11, 22).

FIGS. 4A-4L illustrate exemplary steps of a method of implanting the humeral stem and inclination component of the system 200 of the present invention (and prior to wound closure):

FIGS. 4A-4C: Once the resection protector has been removed, the humeral implant 100 is manually opened to its maximum position (FIG. 4B) and the stem 2 is inserted into the humeral canal of resected humerus 250 (FIG. 4C).

FIG. 4D: A pointed stem impactor 51 is placed into the dimple on the lateral portion of the stem 2. The stem is impacted as far as possible; change to the angled morse taper stem impactor.

Figure 4E:
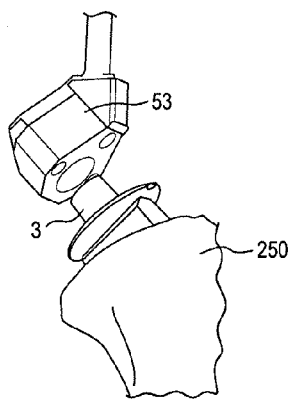
Figure 4F:
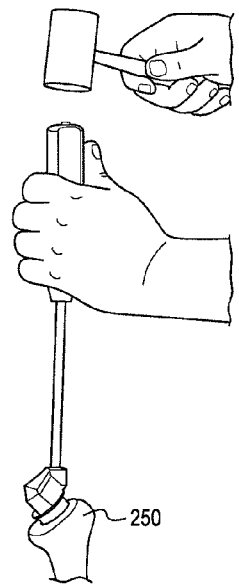

FIGS. 4E and 4F: An angled morse taper stem impactor 53 is placed over the morse taper and impaction is completed. The inclination angle remains free while the stem 2 is impacted into the humerus 250 (FIG. 4F). The inclination angle is established when the flange contacts the humeral surface and is fully seated. For cemented application, the surgeon may select a humeral stem one size smaller than the canal preparation.

Figure 4G:
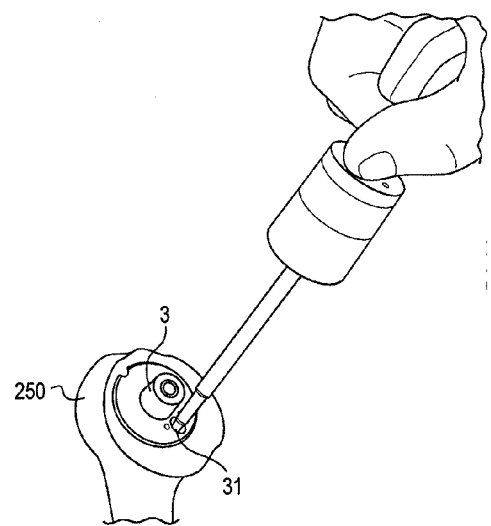

FIG. 4G: The inferior locking screw 31 located on the medial portion of the trunion 3 is tightened. The inferior (inclination) locking screw should be locked before the superior (version) screw is locked.

Figures 4H, 4I:
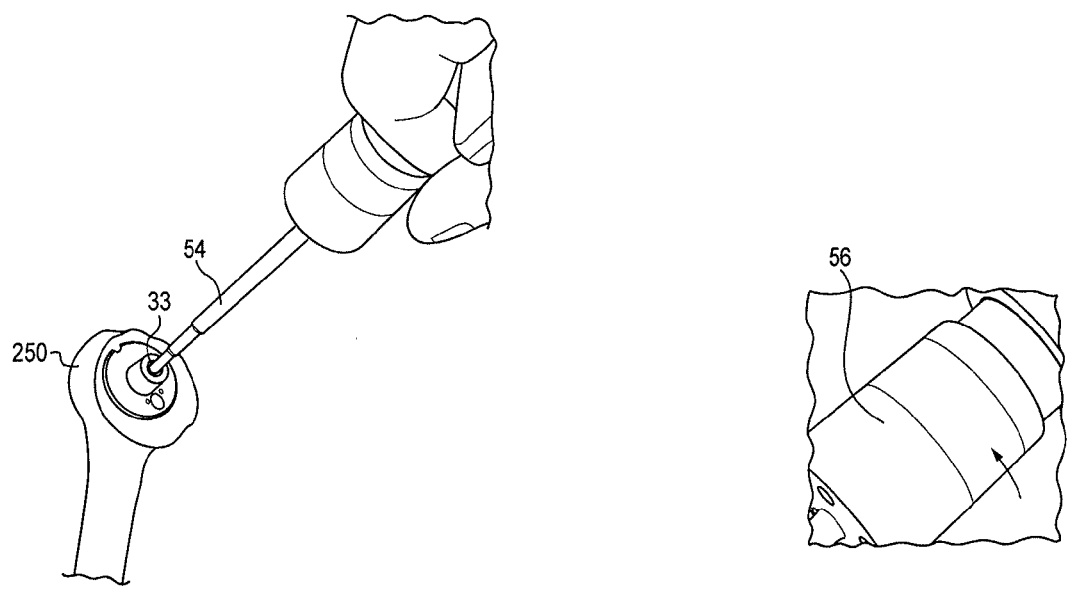

FIGS. 4H and 4I: A torque driver 54 is used to lock the version (superior) screw 33 located on the morse taper of the humeral stem. The surgeon should ensure that the set screw is properly tightened by visually confirming that the "SUP" mark 56 (FIG. 4I) is rotated to the indicator line on the torque driver 54.

Figure 4J:
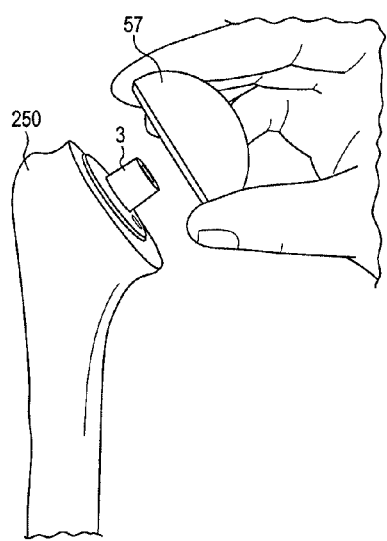
Figure 4K:
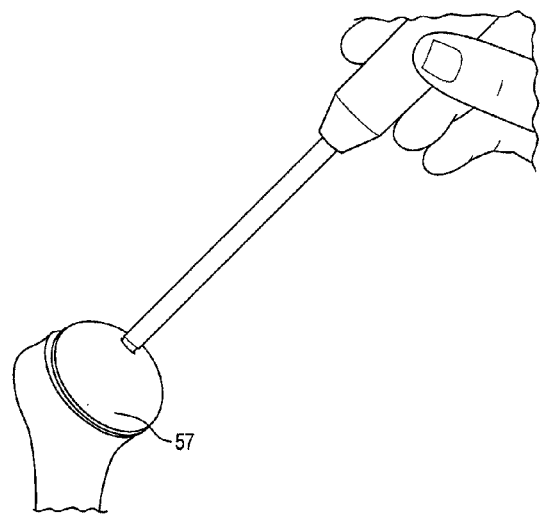

FIGS. 4J and 4K: An appropriate trial head 57 is attached and the trial driver is used to adjust offset. A trial reduction is performed. The position of maximum offset is designated by a line on the surface of the trial head.

Figure 4L:
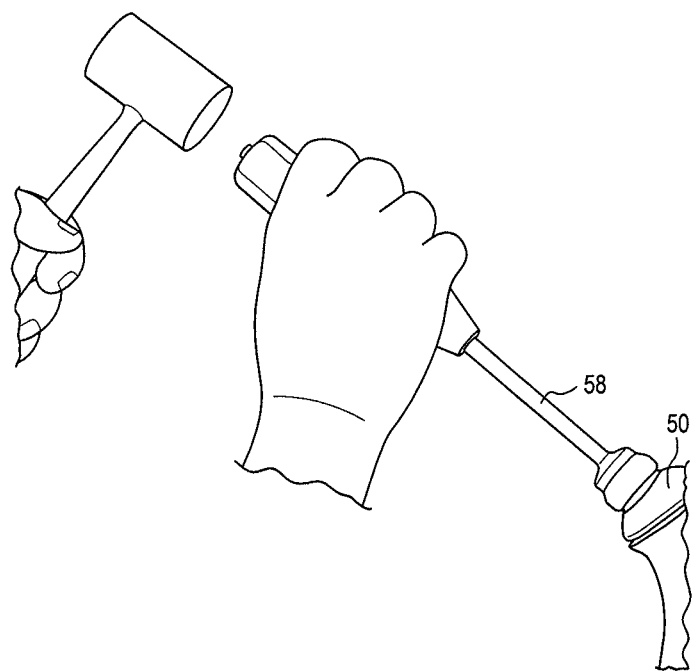

FIG. 4L: After the trial reduction, the trial head 57 is removed and an implant head 50 is impacted onto the humeral stem 2 using the head impactor 58.

Subsequent to the humeral stem implantation, wound closure is conducted (for example, by a Subscapularis Apex Bridge Repair (SABER) technique) to employ the suture holes in the proximal body of the stem (for soft tissue repair and subscapularis closure).

Wound Closure

Wound closure begins by removing any remaining soft tissue or bony debris. Hemostasis may be obtained with electrocautery. The initial focus of wound closure is the repair of the subscapularis tendon 80. To ensure that the subscapularis tendon is repaired to its anatomic position, the first step of the repair is reattaching the superior lateral edge of the subscapularis to the anterior lateral edge of the supraspinatus directly over the bicipital groove. This is performed with a plurality of flexible strands such as #2 FiberWire® sutures. By securing the superior lateral edge of the subscapularis 80 at the beginning of the repair, the tendon is held in an anatomic position.

Four flexible strands (for example, four braided #5 FiberWire® sutures) which were placed at the rim of the osteotomy site are individually passed through the subscapularis tendon 80 separated by approximately 1 cm. The sutures can be passed with a Mason-Allen configuration to improve security of the suture in the tendon. The sutures are tied beginning superiorly and proceeding inferiorly. Additional #2 FiberWire® sutures are placed in between each of the #5 FiberWire® sutures for a tendon-to-tendon repair, reattaching the subscapularis tendon to the remaining fibers in the lesser tuberosity. A total of eight sutures, four #2 FiberWire® sutures for the tendon-to-tendon repair, and four #5 FiberWire® sutures for a tendon-to-bone repair are used for a secure subscapularis repair. This will allow for an early range of motion program and minimize the risk of subscapularis rupture.

The deltoid and pectoralis major muscle may be repaired with a side-to-side closure using another flexible strand such as a #1 absorbable suture. The subcutaneous layer is repaired with an absorbable suture and, finally, another suture is used for the skin closure.

Figure 5A:
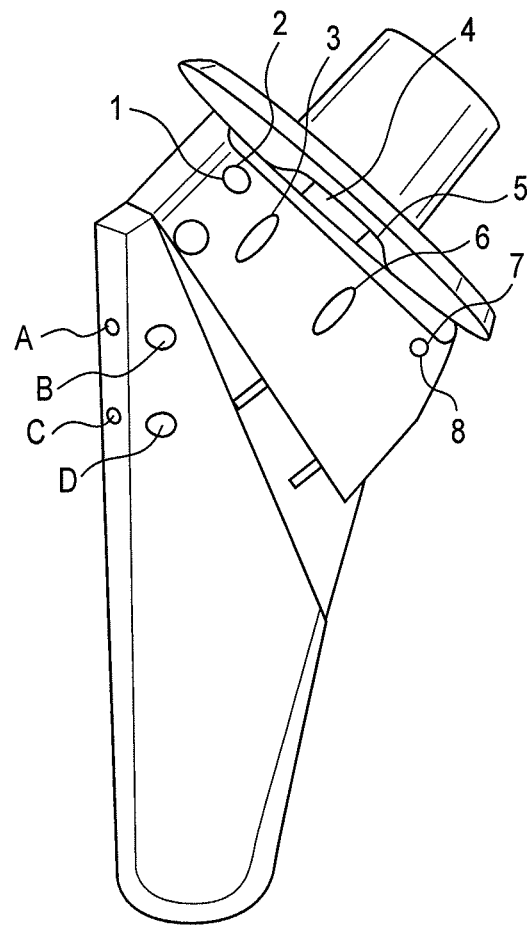
FIGS. 5A-5C illustrate a SABER repair (Subscapularis Apex Bridge Repair or SABER technique) with subscapularis repair and with the exemplary humeral component of FIG. 1B and after the humeral stem implantation.
Figure 5B:
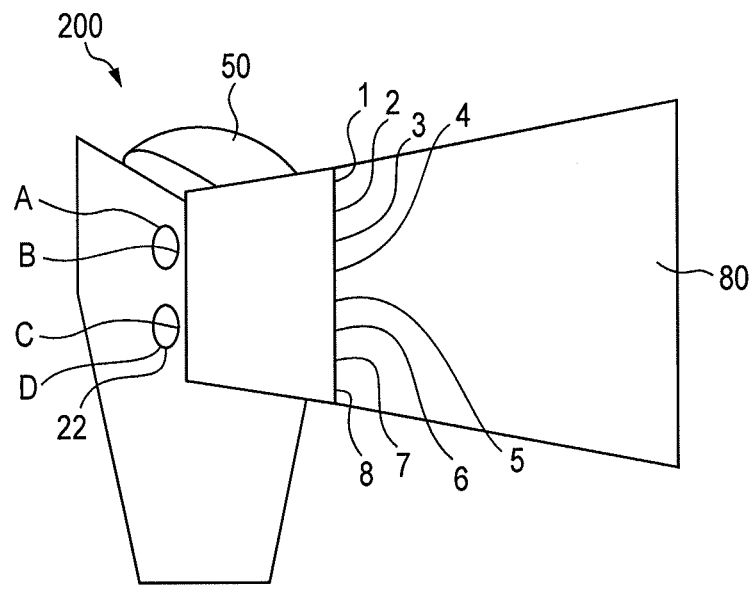
Figure 5C:
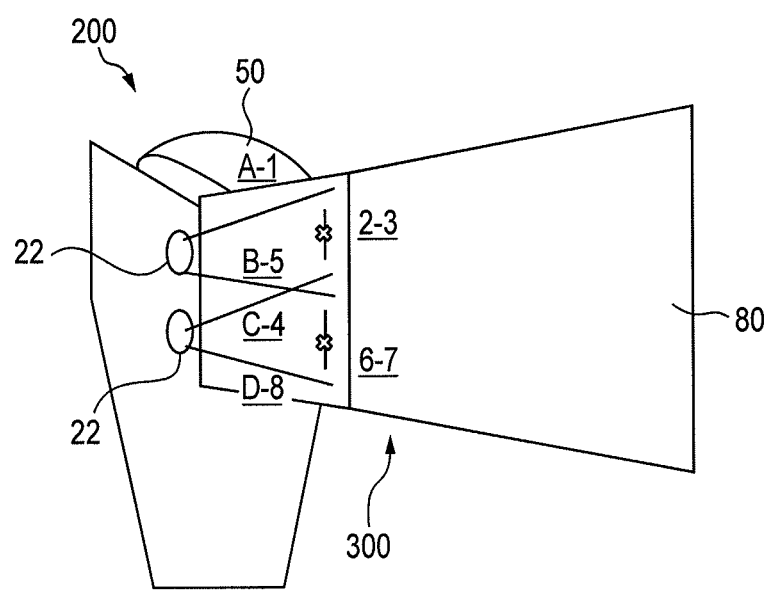

FIGS. 5A-5C illustrate schematic steps of tying sutures through the suture eyelets 11, 22 of the prosthesis 200 of the present invention and according to an exemplary SABER technique to obtain final repair 300 (FIG. 5C).

Subscapularis Apex Bridge Repair (SABER) Technique

FIG. 5A

1) Two holes are drilled vertically in the biceps groove for passage of the lateral suture limbs.
2) Two flexible strands (for example, #2 FiberWire® sutures) are passed through the lateral holes yielding four suture limbs labeled A through D from superior to inferior.
3) Four flexible strands (for example, #2 FiberWire® sutures) are passed through the medial holes yielding eight suture limbs labeled 1 through 8 from superior to inferior.
4) Limbs A&B are passed through the superior hole from the intramedullary canal out. Likewise, limbs C&D are passed through the inferior hole from the intramedullary canal out.
5) All strands are held out to length on tension as the stem is implanted and impacted with the straight impactor followed by the trunion impactor which places the trunion flush to the osteotomy surface.

The inclination (inferior) and version (superior) screws 31, 33 are then tightened with the torque driver.

Trial heads 57 verify proper head size, head offset, shoulder motion, and stability prior to impacting the actual head component.

FIG. 5B

6) Suture limbs 1 through 8 are evenly placed through the medial aspect of the subscapularis tendon 80 from superior to inferior.
7) The sutures are then tied in the follow sequence (FIG. 5C):
   a. 1 to A
   b. 8 to D
   c. 4 to C
   d. 5 to B
   e. 2 to 3 (these sutures will compress the tendon repair to the LT)
   f. 6 to 7 (these sutures will compress the tendon repair to the LT)

The repair 300 is then evaluated by externally rotating the arm with the arm adducted. The degree of external rotation achieved without stressing the repair is noted for post-operative therapy limitations.

In summary, as described above, the humeral component 100 of the present invention which is provided with suture holes 22, 11 incorporated into stem 2 and inclination component 1 may be employed for exemplary subscapularis and supraspinatus repairs, and SST repairs. The stem has a length of about 60 mm. As detailed above, suture eyelets for subscapularis and supraspinatus repairs are incorporated at least into the inclination components (and preferably both into the inclination component and also the stem).

Figure 6A:
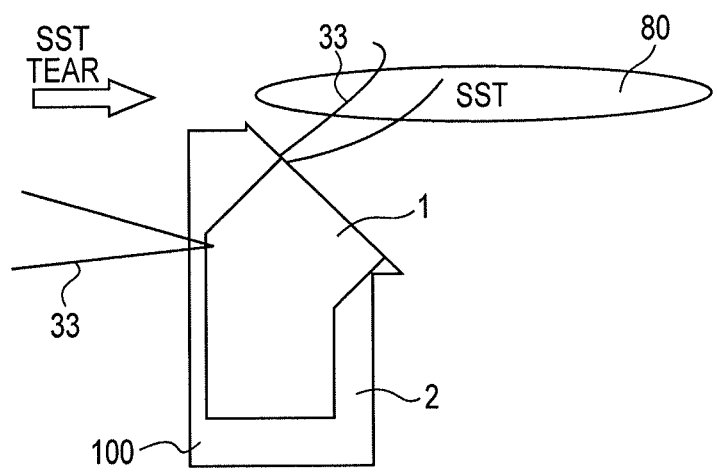
FIGS. 6A-6C illustrate exemplary schematic steps of a method of suture bridge repair according to another embodiment of the present invention.
Figure 6B:
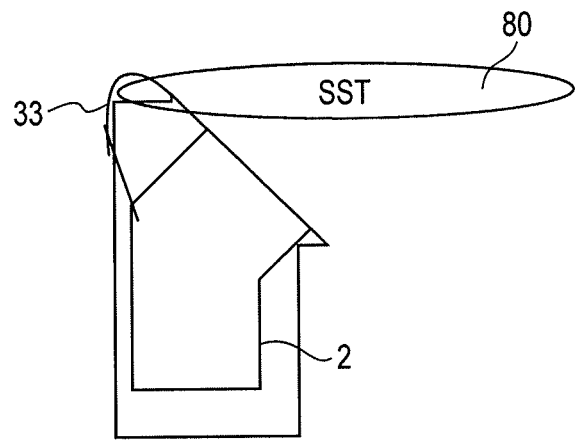
Figure 6C:
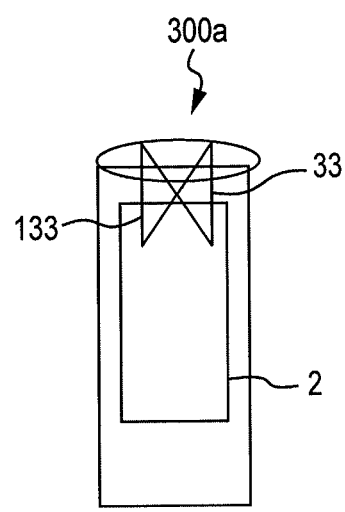

FIGS. 6A-6C illustrate exemplary schematic steps of a method of suture bridge repair with humeral prosthesis 100 with lateral holes 22 and medial holes 11 and flexible strand 33 (suture 33). The steps refer to an SST repair 300a (Simple Shoulder Test repair 300a) with a schematic humeral component 100 and illustrate how the SST repair is conducted with suture bridge configuration 133 (FIG. 6(c)) using anterior and posterior superior-lateral holes. FIG. 6C shows a lateral view of the final, completed SST repair 300. Multiple suture eyelets 11, 22 allow passing of flexible strands 33 (suture strands 33) and more optimal and anatomical locations and repairs for subscapularis and lesser tuberosity attachment. The repair may have vertical, horizontal and crossed sutures 33 for compression of soft tissue 80.

Figure 7A:
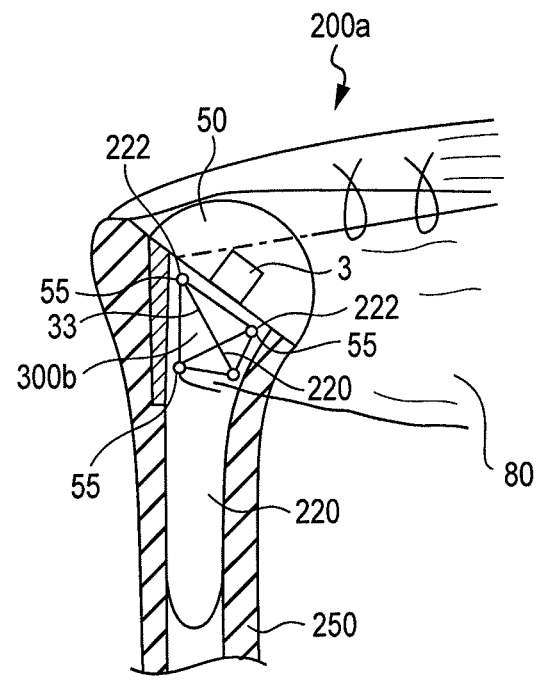
FIG. 7A illustrates a short stem (mini stem) humeral prosthesis according to another embodiment of the present invention (and attached to humerus).
Figure 7B:
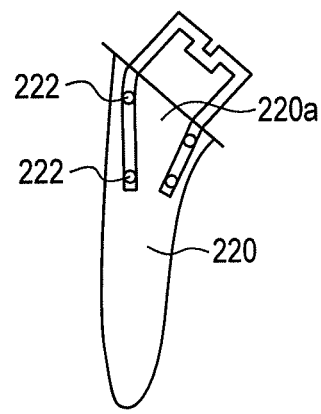
FIG. 7B illustrates a schematic view of the short stem prosthesis of FIG. 7A.

FIGS. 7A and 7B illustrate prosthetic 200a with another mini stem (short stem) 220 of the present invention that provides a stable subscapularis repair and is inserted into resected humerus 250. Stem 220 is provided with a plurality of suture anchor screw holes 222 incorporated into the stem (into upper shank portion 220a of the stem) for receiving a suture anchor to attach tissue. FIG. 7(a) also shows an X box/bridge type repair 300b (a suturing pattern with an X configuration) of the subscapularis 80 with two exemplary rows of compression using fixation devices 55 (for example, anchors 55) with suture 33 (for example, #2 FiberWire® suture 33). This embodiment allows at least part of the holes to be used with suture anchors to attach at least one flexible strand (at least one suture strand, for example) and tissue.

Mini stem 2, 220 of the present invention may be reusable, may be used with osteotomy, tenotomy and/or labral repairs and may peel off (take down). The flexible material 33 (suture 33) may be employed for additional biceps repairs as well and if desired. The mini stem 2, 220 is designed to facilitate ease of revision and to provide a universal platform to restore/accommodate proximal humeral anatomy, as detailed below.

An exemplary method of shoulder repair with short stem 220 of FIGS. 7A and 7B includes inter alia the steps of: (i) use a targeting device placed on the Morse taper 3b to insert screw; (ii) anchor targeting device into screw holes for version/inclination; and (iii) drill guide and insertion guide for screws (anchors 55). The technique may be used to revise failed subscapularis repairs.

Any type of flexible material or suture (such as FiberWire®, FiberTape®, FiberChain®, etc.) may be passed through the eyelets 11, 22 to complete the various soft tissue repairs.

Flexible strands or cords 33 may be made of any known suture construct, such as multifilament, braided, knitted, woven suture, or including fibers of ultrahigh molecular weight polyethylene (UHMWPE) or the FiberWire® suture (disclosed in U.S. Pat. No. 6,716,234 the disclosure of which is hereby incorporated by reference in its entirety herewith). FiberWire® suture is formed of an advanced, high-strength fiber material, namely ultrahigh molecular weight polyethylene (UHMWPE), sold under the tradenames Spectra (Honeywell) and Dyneema (DSM), braided with at least one other fiber, natural or synthetic, to form lengths of suture material. The preferred FiberWire® suture includes a core within a hollow braided construct, the core being a twisted yarn of UHMWPE.

The strands may be also formed of a stiff material, or combination of stiff and flexible materials, depending on the intended application. The strands may be also coated and/or provided in different colors.

Although the present invention has been described in relation to particular embodiments thereof, many other variations and modifications and other uses will become apparent to those skilled in the art. While the present embodiments are described herein with reference to illustrative figures for particular applications, it should be understood that the embodiments are not limited thereto. Those having ordinary skill in the art and access to the teachings provided herein will recognize additional modifications, applications, embodiments and substitution of equivalents falling within the scope of the presented embodiments. Accordingly, the embodiments are not to be considered as limited by the foregoing description.

What is claimed as new and desired to be protected by Letters Patent of the United States is:

1. A method of shoulder repair, the method comprising the steps of:
   providing a humeral prosthetic comprising:
      a humeral stem adapted to be introduced into a patient's humerus, the stem having an upper stem portion, a longitudinal axis, and a first plurality of eyelets within the upper stem portion and disposed about parallel to the longitudinal axis of the humeral stem;
      an elongated inclination component coupled to the upper stem portion of the humeral stem, said elongated inclination component provided with an opening to provide access to a screw to set and fix a position of the inclination component at an inclination angle in relation to the humeral stem, the inclination component further including a second plurality of eyelets provided within the inclination component and disposed about parallel to a longitudinal axis of the inclination component, the inclination component further having an elongate convex surface;
      a coupling adapter including means for setting a version the coupling adapter comprising a plate and an elongated concavity formed on a side of the plate, the elongate concavity complementing the elongate convex surface of the inclination component; and
      a spherical head including means for setting and fixing a radial offset, wherein the humeral stem interfaces with the coupling adapter via said elongated inclination component, and the coupling adapter interfaces with the spherical head;
   providing the humeral prosthetic within a patient's humerus;
   attaching soft tissue to the humeral prosthetic by employing the first and second plurality of eyelets;
   passing first sutures through the first plurality of eyelets;
   passing second sutures through the second plurality of eyelets;
   implanting the humeral prosthetic into the patient's humerus, so that the stem interfaces with the coupling adapter, and the coupling adapter interfaces with the spherical head;
   placing the second sutures through a medial aspect of the soft tissue in a direction from superior to inferior; and tying the first sutures with the second sutures to compress the soft tissue.

2. The method of claim 1, further comprising independently adjusting the radial offset of the spherical head, the inclination angle of the humeral stem, and the version of the adapter.

3. The method of claim 1, wherein the soft tissue is supraspinatus, subscapularis or biceps tendon.

4. The method of claim 1, wherein the humeral stem has a length of about 60 mm.

* * * * *